United States Patent
Van Bommel et al.

(10) Patent No.: US 10,113,698 B2
(45) Date of Patent: Oct. 30, 2018

(54) LIGHTING ASSEMBLY EMITTING A PORTION OF UV LIGHT

(71) Applicant: PHILIPS LIGHTING HOLDING B.V., Eindhoven (NL)

(72) Inventors: Ties Van Bommel, Eindhoven (NL); Rifat Ata Mustafa Hikmet, Eindhoven (NL)

(73) Assignee: PHILIPS LIGHTING HOLDING B.V., Eindhoven (NL)

( * ) Notice: Subject to any disclaimer, the term of this patent is extended or adjusted under 35 U.S.C. 154(b) by 0 days.

(21) Appl. No.: 15/737,149

(22) PCT Filed: Jun. 13, 2016

(86) PCT No.: PCT/EP2016/063486
§ 371 (c)(1),
(2) Date: Dec. 15, 2017

(87) PCT Pub. No.: WO2016/202736
PCT Pub. Date: Dec. 22, 2016

(65) Prior Publication Data
US 2018/0180226 A1 Jun. 28, 2018

(30) Foreign Application Priority Data
Jun. 16, 2015 (EP) ..................... 15172409

(51) Int. Cl.
*F21K 9/232* (2016.01)
*F21K 9/237* (2016.01)
(Continued)

(52) U.S. Cl.
CPC .............. *F21K 9/237* (2016.08); *F21K 9/232* (2016.08); *F21K 9/62* (2016.08); *F21K 9/64* (2016.08);
(Continued)

(58) Field of Classification Search
CPC .................................................. F21Y 2113/10
See application file for complete search history.

(56) References Cited

U.S. PATENT DOCUMENTS 6,501,084 B1 * 12/2002 Sakai ........................ F21K 9/00
250/504 R
2002/0084748 A1 7/2002 Ayala et al.
(Continued)

FOREIGN PATENT DOCUMENTS

CN 202419518 U 9/2012
CN 203810092 U 9/2014
(Continued)

*Primary Examiner* — Alexander K Garlen

(57) ABSTRACT

A lighting assembly (100), a lamp, a retrofit light bulb, a retrofit light tube, a luminaire and a method of illuminating a space are provided. The lighting assembly (100) comprises a first light emitting element (110), a second light source (108) and a reflection element (216). The first light emitting element (110) is for emitting visible light (112) having a color point close to the black body line. The second light emitting element (108) emits UV light (106) in a spectral range from 280 nm to 350 nm. The lighting assembly (100) is configured to emit, in operation, a safe amount of the UV light (106) in the spectral range through a light exit window (102). A ratio between a first radiant flux of the UV light (106) and a second radiant flux of the visible light (112) is in a range from 0.01 to 0.0001.

13 Claims, 7 Drawing Sheets

(51) Int. Cl.
*F21K 9/62* (2016.01)
*F21K 9/64* (2016.01)
*F21V 3/00* (2015.01)
*F21V 7/22* (2018.01)
*H01L 25/075* (2006.01)
*H01L 33/50* (2010.01)
*F21V 9/30* (2018.01)
*H01L 33/60* (2010.01)
*F21Y 101/00* (2016.01)
*F21Y 115/10* (2016.01)
*F21Y 113/13* (2016.01)
*F21V 3/10* (2018.01)

(52) U.S. Cl.
CPC ............... *F21V 3/00* (2013.01); *F21V 7/22* (2013.01); *F21V 9/30* (2018.02); *H01L 25/0753* (2013.01); *H01L 25/0756* (2013.01); *H01L 33/507* (2013.01); *F21V 3/10* (2018.02); *F21Y 2101/00* (2013.01); *F21Y 2113/13* (2016.08); *F21Y 2115/10* (2016.08); *H01L 33/60* (2013.01)

(56) References Cited

U.S. PATENT DOCUMENTS

| | | |
|---|---|---|
| 2010/0007267 A1 | 1/2010 | Imai et al. |
| 2014/0299793 A1 | 10/2014 | Deng |
| 2015/0014715 A1 | 1/2015 | Hsing Chen et al. |
| 2017/0303523 A1* | 10/2017 | Sandford ................. F21V 3/00 |

FOREIGN PATENT DOCUMENTS

| | | |
|---|---|---|
| DE | 202010004777 U1 | 9/2011 |
| JP | 2001243821 A | 9/2001 |
| JP | 2006525684 A | 9/2006 |
| JP | 2007103511 A | 4/2007 |
| JP | 2010027645 A | 4/2010 |
| JP | 2014222705 A | 11/2014 |
| TW | 201032705 A | 9/2010 |
| WO | WO2013180890 A1 | 12/2013 |
| WO | WO2014088298 A1 | 6/2014 |
| WO | WO-2015173770 A2 * | 11/2015 .......... F21V 33/0092 |

* cited by examiner

LIGHTING ASSEMBLY EMITTING A PORTION OF UV LIGHT

CROSS-REFERENCE TO PRIOR APPLICATIONS

This application is the U.S. National Phase application under 35 U.S.C. § 371 of International Application No. PCT/EP2016/063486, filed on Jun. 13, 2016, which claims the benefit of European Patent Application No. 15172409.3, filed on Jun. 16, 2015. These applications are hereby incorporated by reference herein.

FIELD OF THE INVENTION

The invention relates to a lighting assembly.

The invention further relates to a lamp, a retrofit light bulb, a retrofit light tube, a luminaire and a method of illuminating a space.

BACKGROUND OF THE INVENTION

US patent application US2002/0084748A1 discuses a light source that is suitable for general illumination, which means for the illumination of spaces that may be too dark for people to stay or work in. The light source comprises a light emitting diode (LED) that emits UV light. Phosphor material is used to convert the phosphor material towards visible light that is emitted into the ambient for illuminating the environment. Near a light exit window, a material is provided that reflects non-converted UV light back to the phosphor material for conversion such that no UV light is emitted into the ambient.

SUMMARY OF THE INVENTION

It is an object of the invention to provide an improved light source for illumination of a space and to provide an improved method for illumination of a space.

For this purpose, according to an aspect of the invention, a lighting assembly is provided. For this purpose, according to other aspects of the invention, a lamp, a retrofit light bulb, a retrofit light tube and a luminaire are provided. For this purpose, according to yet another aspect of the invention, a method of illuminating a space is provided.

The lighting assembly comprises a light exit window, a first light emitting element, a second light source and a reflection element. The light exit window is for emitting light into an ambient of the lighting assembly. The first light emitting element emits, in operation, visible light. The first light emitting element is capable of emitting visible light that has a color point in a CIE XYZ color space and this color point has, in this color space, a distance smaller than 25 SDCM to the black body line. The second light source emits, in operation, UV light. The UV light comprises light in a spectral range from 280 nm to 350 nm. The second light source is arranged not to emit the UV light directly towards the light exit window. The reflection element reflects UV light and is arranged at a position where it receives at least a portion of the UV light and reflects the received UV light towards the light exit window. In use, the UV light is at least partly emitted through the light exit window. The lighting assembly is configured to emit, in operation, an amount of the UV light in the spectral range through the light exit window. The amount of the UV light has a first radiant flux. The lighting assembly is configured to emit a second radiant flux of the visible light through the light exit window. A ratio between the first flux and the second flux is in a range from 0.01 to 0.0001.

The lighting assembly emits visible light that is well-suitable for illumination. The first light emitting element is capable of emitting relatively white light which is in particular suitable for illumination. In specific embodiment, the first light emitting element may comprise controllable light emitters emitting different colors. In this specific embodiment it is possible to control the light emitter to emit a mix of the different colors that has the color point, as defined, relatively close to the black body line. In another embodiment, the first light emitting element always emits, in operation, the visible light having the color point within the defined maximum distance to the black body line. In other words, when the first light emitting element is capable of emitting the visible light having the defined color point, it is not necessary that the first light emitting element always emits such light, but it means that the first light emitting element is at least in some operational modes capable of emitting the light with such a color point.

As defined by the distance to the black body line, the visible light may be exactly white light or slightly off-white light. Within these specific situations, the visible light is still relatively white to obtain a good illumination of the space and, for example, to have a relatively good color rendering. It is to be noted that, in specific embodiments, the visible light has a color point within 7 SDCM, or 5 SDCM, from the black body line. The visible light is emitted by the first light emitting element. It is to be noted, as will be discussed later in this document, that the first light emitting element may be a first light source or may comprise one or more luminescent materials, which converts the UV light to the visible light.

The light assembly also emits UV light through the light exit window. Thus, not only the visible light illuminates the environment, in which the lighting assembly is operated, the UV light also illuminates the environment. Humans, who are in this environment, receive a specific amount of UV light in the spectral range from 280 nm to 350 nm. This spectral range comprises the so-termed UV-b spectral range (280 nm-315 nm) and a portion of this spectral range is outside this range. Humans, who do not receive any natural sunlight on their skin, often lack a large enough Vitamin D production—the UV light in the spectral range stimulates the production of Vitamin D in the human skin and, as such, health benefits are obtained. On the contrary, it is also known that the reception of too much UV light by the human skin may cause, for example, skin cancer in the middle long or long term. The amount of emitted UV light is relatively low compared to the amount of emitted visible light. Thereby, it prevents human skin to receive too much UV light resulting in possible health risks.

The reflection element is arranged at a position where it receives, in operation, at least, a portion of the UV light and is arranged to reflect, in operation, the portion of the UV light towards the light exit window. The second light source is arranged not to emit the UV light directly towards the light exit window. For example, the second light source emits a light beam; and the position as well as direction of the second light source in which it emits the light, is chosen such that the UV light is emitted towards the reflection element. The amount of emitted UV light is relatively low to prevent possible health risks. However, close to the second light source, the irradiance (light energy per area unit) of UV light may be relatively high. It might be that, as a result of misuse, the human naked eye or other sensitive parts of the human body may come very close to the second light source receiving a too high irradiance of UV light, causing damage. When the light emitted by the second light source is reflected, at least, once, the light beam emitted by the second light source becomes, at least, several times wider (seen in a cross-sectional size of the light beam into a plane perpendicular to the light beam) than directly at the light emitting surface of the second light source and thereby, the irradiance reduces quite a lot. Thus, by forcing that the UV light is not directly emitted into the ambient of the lighting assembly, but is only emitted into the ambient after one reflection, the lighting assembly is safer under misuse conditions.

In general there is a prejudice to prevent the emission of UV light towards humans with artificial light sources to prevent the possible health issues. When too much UV light falls on the human skin, it can cause, for example, skin cancer in the middle long or long term. For example, in the field of illumination, US patent application US2010/0007267A1 proposes to use a fluorescent film to convert all UV radiation to visible light, or to use a UV cutting film that absorbs UV light. The above discussed US patent application US2002/0084748A1 discloses also a light to be used for illumination and has measures to prevent the emission of UV light into the embodiment.

Despite the above prejudice, some light sources may emit UV light and visible light simultaneously. Also these light sources confirm the above discussed prejudice because they are specifically designed to prevent the emission of UV light towards humans. US patent application US2014/0299793A1 discloses a method of disinfection and a lighting device for use in this method. The lighting device comprises two types of Light Emitting Diodes (LEDs), one type for emitting UV light and one type for emitting visible light. Both types of light can be emitted by the lighting device and, in particular, the UV light is used for killing bacteria. In order to achieve the bacteria killing effect, the amount of UV light that must be emitted is relatively large, which might be dangerous for humans. In order to prevent possible health issues for the operator of the lighting device, the LEDs are surrounded by a reflector such that, under normal operational conditions, no UV light is emitted towards a person that is operating the lighting device. In another example of Chinese utility model CN203810092U, UV light and visible light can be emitted by the disclosed flaw detection lamp. This flaw detection lamp is also arranged to emit, in operation and under normal operational conditions, the UV light away from the operator.

In certain applications it is accepted to expose the human skin for a limited amount of time to UV light. One application is, for example, tanning the skin with artificial light. Specific light sources, the so-termed tanning lamps, are developed for tanning beds. Such tanning lamps emit a significant amount of both UV light and visible light. These light sources are not suitable for illumination, because it would induce too much health risks for a person, who stays in that space for relatively long periods of time.

Thus, there is a prejudice to exposing humans to artificial UV light. Despite the prejudice, the inventors have found a lighting assembly that emits a combination of UV light and visible light and that is suitable for illumination. The inventors of the lighting assembly have carefully considered the possible health risks and possible health benefits. They have found which UV light is suitable for this application and they have found an advantageous range of ratios between the emitted UV light and the emitted visible light, in which the health benefits certainly outweigh possible risks.

Optionally, the first light emitting element is a first light source being capable of emitting the visible light or the first light emitting element is a luminescent element being capable of converting a portion of the UV light towards the visible light. The luminescent element comprises one or more luminescent materials, such that the combination of the luminescent materials absorbs the portion of the UV light and has a combined light emission that is the visible light. In certain applications, it may be advantageous to have only one type of light source that emits UV light, which is partially converted towards the visible light. A mix of luminescent materials may result in, for example, a relatively high color rending index (CRI). This may be advantageous if the price of UV emitting light sources outweighs the price of the luminescent materials.

It is to be noted that a mix of luminescent materials and light sources that emit light in the visible spectral range may be used to generate the visible light as well.

Optionally, the relative positions of the second light source, the reflection element, and the light exit window are selected such that an irradiance of the UV light remains below $10^{-3}$ W/m$^2$ along the whole light exit window. At this irradiance level, the lighting assembly is relatively safe. The lighting assembly is also relatively safe in misuse scenarios when, for example, the user has one of his eyes very close to the light exit window or the user moves his skin very close to the light exit window.

Optionally, the lighting assembly comprises a dichroic mirror that is configured to reflect the UV light and is configured to transmit the visible light. The dichroic mirror is arranged at a mirror position to prevent the direct emission of UV light from the second light source through the light exit window. If the reflection element is such a dichroic mirror, specific advantageous configuration of elements are possible in the lighting assembly. For example, in an embodiment, the second light source and the first light emitting element may be arranged to emit light towards the light exit window. At the mirror position, in between the light exit window at one side, and the second light source and the first light emitting element at another side, the dichroic mirror is arranged, which allows the emission of the visible light directly towards the light exit window and which reflects the UV light towards the inner walls of the lighting assembly, and subsequently the inner walls reflect the UV light towards the light exit window. In this embodiment, the UV light is reflected twice, which results in a relatively low irradiance for the UV light at the light exit window.

Optionally, a smallest angle, between a first direction of a first light beam emitted, in operation, by the second light source and a second direction of a second light beam emitted, in operation, by the first light emitting element, is between 90 and 180 degrees, or, optionally, between 120 and 180 degrees. Optionally, the second direction is towards the light exit window. In this optional embodiment, the light beams of UV light and of visible light are emitted, in operation, about perpendicular or about opposite to each other. This enforces that, at least, one of the light beams is not directly emitted towards the light exit window and, thus, measures must be taken to reduce the irradiance of one of the types of light (such as discussed in the previous optional embodiments). When the irradiance of the UV light is reduced and when the first direction is away from the light exit window, the lighting assembly is safer.

Optionally, the lighting assembly comprises a light mixing chamber. The light mixing chamber is, at least, partially enclosed by walls. At least a portion of the walls are UV light reflective. The light exit window is provided in the walls. Optionally, the second light source is arranged to emit the UV light towards the walls. In a light mixing chamber, the UV light may be reflected, at least, once before it has been emitted through the light exit window and thereby, creating a relatively safe lighting assembly. Also, the UV light may be emitted more homogeneous along the light exit window and at a large number of light emission angles.

Optionally, the lighting assembly comprises a light guiding space that is arranged substantially parallel to the light exit window. The light guiding space may be filled with light guiding material (or, in other words, the light guide space may be a light guide) or a space that is filled with air (or another material in the gaseous phase) and has at least two opposite sides transparent plates, which guide the light that impinges on the transparent plates at an angle above a certain threshold angle. The light guiding space has, at a wall opposite to the light exit window, UV light outcoupling elements for outcoupling the light guided by the light guiding space towards the light exit window. The outcoupling elements may be UV light reflective areas or irregular structures that change a direction of rays of UV light, and thereby, assisting the outcoupling of the UV light. The second light source is arranged to emit a UV light beam into the light guiding space at a direction substantially parallel to the light exit window. The light guiding space, at least, once reflects the received UV light and creates a relative uniform UV light output along its surface that is facing the light exit window. Thereby, no high irradiance of UV light is locally emitted through the light exit window and thereby, the lighting assembly is relatively safe.

Optionally, the second light source emits in use at least 60% of the emitted UV radiation in the spectral range from 300 nm to 320 nm.

According to an aspect of the invention, a lamp for illumination is provided, which comprises one of the above discussed lighting assemblies. In summary, such a lamp can be used to illuminate a space such that the humans that are present in this space receive a small amount of UV light, which stimulates Vitamin D production. The amount of received UV light is low and, as such, the lamp is relatively safe. The lamp has similar embodiments, effects and advantages as the lighting assembly.

According to an aspect of the invention, a retrofit light bulb for illumination is provided. The retrofit light bulb comprises a light transmitting bulb and one of the above discussed lighting assemblies. The light transmitting bulb comprises an UV light reflective layer at a first portion of the light transmitting bulb, and, at least, a second portion through which visible light and UV light may be transmitted into the ambient. The second portion is configured to be a light exit window. The second light source is arranged to emit the UV light only towards the first portion. The UV light reflective layer acts as the reflection element.

According to an aspect of the invention, a retrofit light tube for illumination is provided. The retrofit light tube comprises a light transmitting tube and one of the above discussed lighting assemblies. The light transmitting tube comprises an UV light reflective layer at a first portion of the light transmitting tube, and at least a second portion through which visible light and UV light may be transmitted into the ambient. The second portion is configured to be a light exit window. The second light source is arranged to emit the UV light only towards the first portion. The UV light reflective layer acts as the reflection element.

The retrofit light bulb and the retrofit light tube can be used in luminaires that are designed to use traditional light bulbs and traditional (fluorescent) light tube. Thereby, it is possible to retrofit those luminaires with light sources that emit a small amount of UV light to stimulate Vitamin D product and which are relatively safe for humans. The retrofit light bulb and the retrofit light tube may have embodiment, effects and advantages similar to the embodiments, effect and advantages of the above discussed lighting assemblies.

According to an aspect of the invention, a luminaire for illumination is provided. The luminaire comprises one of the above discussed lighting assemblies, the above discussed lamp, the above discussed retrofit light bulb or the above discussed retrofit light tube. The luminaire has similar embodiments, effects and advantages as the embodiments, effect and advantages of the lighting assembly, the lamp, the retrofit light bulb and/or the retrofit light tube.

Optionally, the luminaire comprises a luminaire light exit window and a luminaire UV light reflective surface. The UV light reflective surface is arranged to reflect the impinging UV light towards the luminaire light exit window. In so far, this optional embodiment comprises one of the above discussed lighting assemblies or the above discussed lamp, the second light source is arranged to emit the UV light towards the luminaire light reflective surface. Thereby, the lighting assembly or lamp, in combination with the luminaire, provides a relatively safe emission of UV light into the illuminated space because the UV light is reflected, at least, once to reduce the irradiance of the emitted UV light. The luminaire UV light reflective surface acts as the reflection element.

According to an aspect, a method of illuminating a space is provided. The method i) providing a lighting assembly comprising a light exit window for emitting light into an ambient of the lighting assembly, a first light emitting element for emitting visible light, and a second light source for emitting UV light, the first light emitting element being capable of emitting visible light having a color point in a CIE XYZ color space, the color point having a distance smaller than 25 SDCM to the black body line in said color space, the UV light comprising light in a spectral range from 280 nm to 350 nm, ii) emitting a safe amount of UV light in the spectral range through the light exit window, the safe amount of the UV light has a first radiant flux, the UV light is not emitted directly towards the light exit window, iii) reflecting at least a portion of the emitted UV light towards the light exit window, iv) emitting a second radiant flux of the visible light through the light exit window, a ratio between a first radiant flux and a second radiant flux is in a range from 0.01 to 0.0001. The emitting of the UV light and the emitting of the visible light is performed simultaneously and during this simultaneous operation, the ratio is in the defined range.

The method has similar embodiments with similar effects and advantages as the embodiments of the above discussed lighting assemblies, the lamp, the retrofit light bulb, the retrofit light tube and/or the luminaire.

Further preferred embodiments of the assembly, the lamp, the retrofit light bulb, the retrofit light tube, the luminaire and method of illuminating a space according to the invention are given in the appended claims, disclosure of which is incorporated herein by reference.

BRIEF DESCRIPTION OF THE DRAWINGS

These and other aspects of the invention will be apparent from and elucidated further with reference to the embodiments described by way of example in the following description and with reference to the accompanying drawings, in which FIG. 1a schematically presents a cross-sectional view of a lighting assembly.

The figures are purely diagrammatic and not drawn to scale. In the Figures, elements which correspond to elements already described may have the same reference numerals.

DETAILED DESCRIPTION OF EMBODIMENTS

Figure 1A:
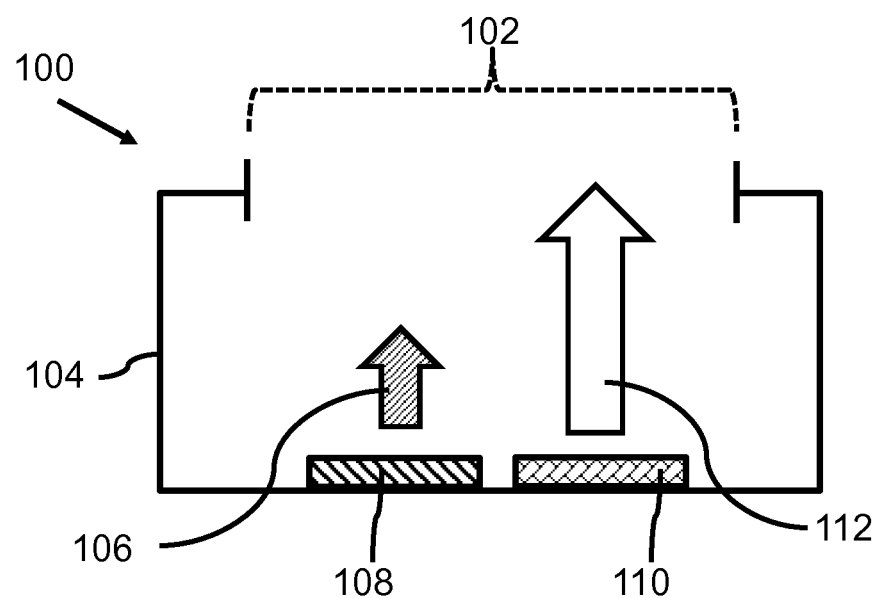
FIG. 1b presents a CIE XYZ color space in which an area is indicated where a color point of the visible light may be located, FIGS. 2a to 2c schematically present cross-sectional views of different embodiments of lighting assemblies, FIGS. 3a to 3c schematically present cross-sectional views of different embodiments of lighting assemblies, FIGS. 4a and 4b schematically present cross-sectional views of a (possibly retrofit) light tube comprising a lighting assembly, FIG. 5a schematically presents a cross-sectional view of a luminaire comprising a lighting assembly, FIG. 5b schematically presents a cross-sectional view of a (possibly retrofit) light bulb, FIG. 6a schematically presents a cross-sectional view of a lighting assembly comprising a light mixing chamber, FIG. 6b schematically presents a three dimensional view of a luminaire, and FIG. 7 schematically presents a method of illuminating a space.

FIG. 1a schematically presents a cross-sectional view of a lighting assembly 100. Lighting assembly 100 is not an embodiment of the invention but is being presented as an introduction to embodiments of the invention. Embodiments of the invention comprise a reflection element as will be discussed in subsequent figures. The lighting assembly 100 comprises an optional housing 104. A light exit window 102 is provided in the housing 104. At a surface of the housing 104, opposite to the light exit window 102, a second light source 108 and a first light emitting element 110 are provided. The second light source 108 is capable of emitting, in operation, UV (Ultra Violet) light 106 in a spectral range from 280 nm to 350 nm. The first light emitting element is capable of emitting, in operation, visible light 112, which is relatively white light having a color point in a CIE XYZ color space and a distance, from the color point to the black body line in this color space, smaller than 25 SDCM (Standard Deviation Colour Matching). In operation, the second light source 108 emits a first radiant flux of the UV light 106 and the first light emitting element emits a second radiant flux of visible light 112 through the light exit window 102. A ratio between the first radiant flux and the second radiant flux is in a range from 0.01 to 0.0001.

The lighting assembly 100 emits visible light 112 that is well-suitable for illumination because it is relatively white light. As defined by the distance to the black body line, the visible light 112 may be off-white light. For example, in specific situations, it is useful to emit bluish white light because it helps people to be more productive, or in other situations, it is useful to emit greenish white light because it helps people to feel more relaxed. The visible light 112 is still relatively white to obtain a good illumination of the space and, for example, to have a relatively good color rendering. It is to be noted that, in a specific embodiment, the visible light 112 has a color point within 7 SDCM, or 5 SDCM, from the black body line. The visible light 112 is emitted by the first light emitting element 110. As will be discussed later, the first light emitting element 110 may be a first light source or may comprise one or more luminescent materials, which convert other light, for example, a portion of the UV light 106 to the visible light 112. Visible light is defined as light that can be seen by humans. In general, visible light has wavelengths in a range from 400 nm to 800 nm. The light emission distribution of the visible light 112 may have some tails outside this range and, optionally, at least 90% of all light, emitted by the first light emitting element, is in the range from 400 nm to 800 nm. Optionally, the visible light 112 has a relatively high Color Rendering Index (CRI), for example, at least 80, at least 85, or at least 90. Optionally, the correlated color temperature (CCT) of the visible light 112 is in the range of 2.000-20.000 K, 2.500-10.000 K, or 2.700-8.000 K.

The light assembly 100 also emits UV light 106 through the light exit window 102. Thus, not only the visible light 112 illuminates the environment in which the lighting assembly 100 is operated, the UV light 106 also illuminates the environment. Humans, who are in this environment, receive a specific amount of UV light 106 in the spectral range from 280 nm to 350 nm. This UV light 106 stimulates the production of Vitamin D in the human skin and, as such, health benefits are obtained. On the contrary, the amount of emitted UV light 106 is relatively low compared to the amount of emitted visible light 112. Thereby, prevents human skin to receive too much UV light 106, resulting is possible health risks. The second light source 108 emits UV light in the defined spectral range. It is possible that the light distribution of the second light source 108 has tails outside the above discussed spectral range and optionally, at least, 75% of the light energy emitted by the second light source 108 is emitted in the spectral range. Optionally, the second light source emits UV light 106 in a range from 290 nm to 340 nm, and, at least, 65% of the light energy emitted by the second light source 108 is emitted in this range from 290 nm to 340 nm. Optionally, the second light source emits UV light 106 in a range from 295 nm to 335 nm, and, at least, 60% of the light energy emitted by the second light source 108 is emitted in this range from 295 nm to 335 nm. Optionally, the second light source emits UV light 106 in a range from 300 nm to 320 nm and at least 55% of the radiant flux emitted by the second light source 108 is emitted in the range from 300 nm to 320 nm. In particular, when the second light source 108 mainly emits UV-b light and the UV-b light is, optionally, concentrated in a relatively small range (e.g. ±10 nm) around 310 nm, the most effective UV light is emitted for stimulating the Vitamin D production by the human skin, and other forms of possibly harmful UV light are not emitted. In this document, when the term "UV light" has been used, UV-b light or one of the above discussed smaller wavelength range is meant and, as discussed above, it is possible that the second light source 108 emits a small amount of UV light outside this range, but the majority of the energy is emitted in the defined range(s).

As discussed above, the amount of UV light 106 emitted through the light exit window 102 is relatively small compared to the amount of visible light 112 emitted through the light exit window 102. This has been defined by means of a ratio of the first radiant flux of the UV light 106 (in the spectral range) through the light exit window 102 and the second radiant flux of the visible light 112 through the light exit window 102. In this context, radiant flux is the radiant energy transmitted through the light exit window. The SI unit of radiant flux is watt (W). Radiant fluxes can be measured by means of a calibrated power meter. The calibrated power meter or spectrometer and the lighting assembly may be placed in an integrating sphere for obtaining a reliable measurement. The power meter or the spectrometer may use filter or gratings to distinguish between different wavelengths. For example, a measurement is performed when the power meter is equipped with a filter which allows the emission of light in between 280 nm and 350 nm. Or, for example, several measurements are used which allow the transmission of different, smaller, ranges and the results of the different measurements are combined to one result. The radiant fluxes may be measured under different operational conditions, for example, when the lighting assembly is controlled to operate at full power and, for example, when the lighting assembly is controlled to operate at 50% of its maximum power. In an embodiment, the first radiant flux and the second radiant flux are determined under predefined operational conditions. The predefined operational conditions are, for example, the conditions that are defined by the manufacturer of the different light emitting components as the ideal conditions to operate the light emitting components. The predefined operational conditions may comprise, at least one of a predefined current provided to the light emitting components, and a predefined voltage provided to the light emitting components, and may also include pre-defined environmental conditionals like the ambient temperature. The ratio between the first radiant flux and the second radiant flux is in between 0.01 and 0.0001. Optionally, the ratio is in between 0.005 and 0.0001. Optionally, the ratio is in between 0.001 and 0.0001.

The lighting assemblies of this document, the lamp, the light bulb, the light tube and the luminaire are for illumination. In the context of this document, "illumination" must be considered as "general illumination", which means, it is not the illumination of an environment or a product with another purpose (killing bacteria, growing plants, detecting cracks, medical treatment, tanning) than just illuminating it. It means that when a space is too dark for people to work/live in, and its illumination level must be raised, the embodiments of this document can be used for the purpose of increasing the illumination level of that space such that it is convenient for people to live and work in that space. In practical embodiments, the lighting assemblies, the lamps, the light bulb, the light tube are capable of emitting at least 300 lumens of light. In practical embodiments, the lighting assemblies, the lamps, the light bulb, the light tube are capable of emitting not more than 2000 lumens of light. Sometimes the light exit window is medium sized (e.g. when a multitude of light sources are used in one lighting assembly). In such cases the light exit window is in between 30 to 300 $cm^2$. In such cases the light output is in between 1000 and 5000 lumens. Luminaires have, in general, also a light output in between 1000 and 5000 lumens of light and their luminaire light output window has often predefined fixed sizes, for example, 50×50 cm, 60×60 cm or 60×120 cm. Thus the luminaire light output windows are in general in between 2500 $cm^2$ and 7200 $cm^2$.

In the context of FIG. 1a, it is to be noted that FIG. 1a only shows one second light source 108 and one first light emitting element 110. In practical embodiments more than one second light source 108 and more than one first light emitting element 110 may be used. The second light source 108 emits the UV light 106 in the range from 280 nm to 350 nm. The first light emitting element 110 may comprise a first light source that emits the visible light 112. Such a first light source may be a single light emitter or may comprise a group of light emitters, for example, a red light emitter, a blue light emitter and a green light emitter, or for example, several light emitters that are capable of emitting the visible light 112. When the first light emitting element comprises a first light source, this first light source may also comprise luminescent material which converts light generated by a light emitter towards at least a portion of the visible light 112. The first light emitting element 110 may also include one or more luminescent materials for performing light emission. For example, the luminescent materials absorb a portion of the UV light 106 emitted by the second light source 108 and convert the absorbed light towards the visible light 112. The first light emitting element may comprise a mix of luminescent materials. These luminescent materials may all be capable of absorbing UV light, and in another embodiment, one of the luminescent materials may convert UV light towards another color of light (e.g. blue light) and the other luminescent materials may partially convert the another color of light towards yet other colors of light (e.g. red and green light).

In the above description, one or more second light sources and, optionally, one or more first light sources are discussed. The second light source and/or the first light source may be a solid state light emitter such as, for example, a Light Emitting Diode (LED), an Organic Light Emitting diode (OLED), or, for example, a laser diode. The second light source and/or the first light source may also be other types of light sources, such as, for example, incandescent lamp or a gas-discharge lamp. In the context of this document it is relevant that the respective light sources are configured to emit a specific type of light, such as the UV light or the visible light having a color point close to the black body line.

Figure 1B:
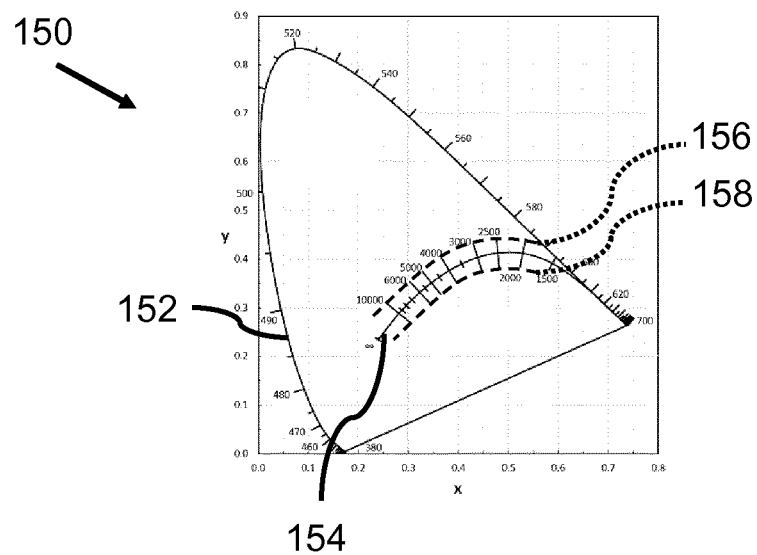

FIG. 1b presents a CIE XYZ color space 150, in which an area between lines 156 and 158 is indicated, where a color point of the visible light may be located. In the CIE XYZ color space 150, a line 152 is drawn, which represents the color point of light of a single wavelength and a black body line 154 is drawn. The black body line 154 represents color points of electromagnetic radiation emitted by black bodies having a specific temperature. In general, light with color points on the black body line 154 are experienced by humans as substantially white light. Light, at a maximum distance of 25 SDCM, is still experienced by the human naked eye as relatively white with a slight color tint. The area, with a maximum distance of 25 SDCM, is schematically indicated in FIG. 1b as the area between lines 156 and 158.

Above discussed characteristics and embodiments of the UV light 106, the visible light 112, the second light source 108 and the first light emitting element 110 do also apply to the same type of elements of the embodiments of FIGS. 2 to 6 unless stated otherwise.

Figure 2A:
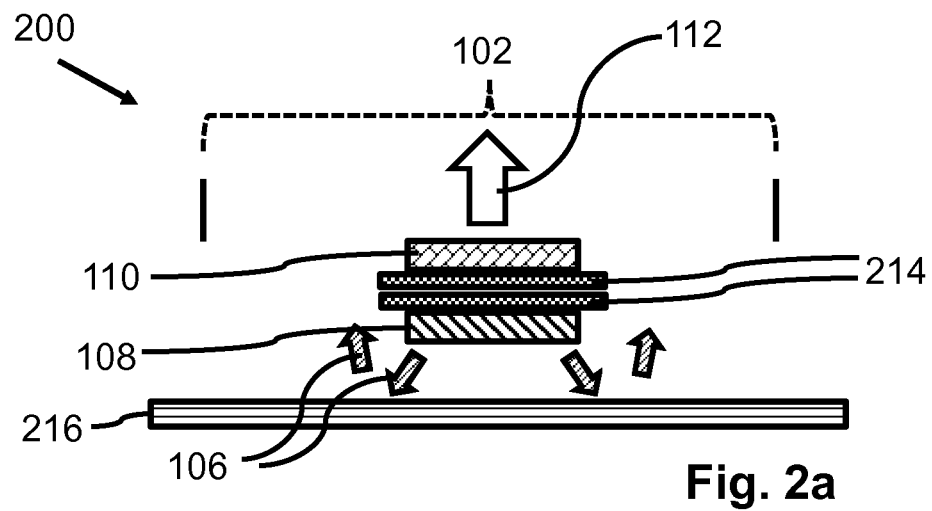
Figure 2B:
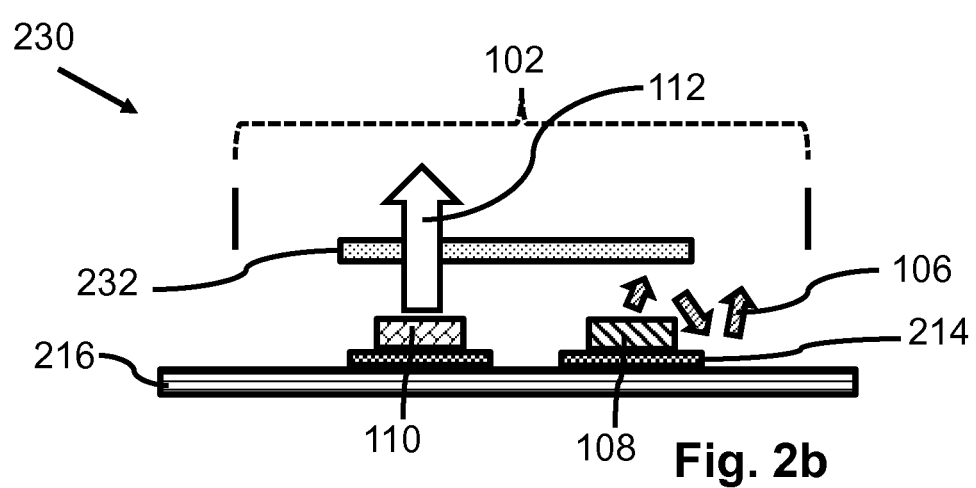
Figure 2C:
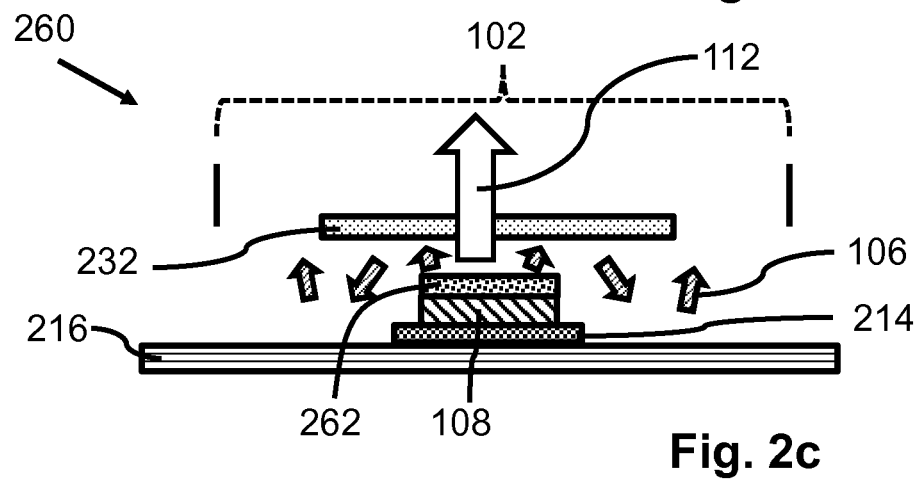

FIGS. 2a to 2c schematically present cross-sectional views of different embodiments of lighting assemblies 200, 230, 260.

FIG. 2a schematically shows light exit window 102. In front of the light exit window 102, the first light emitting element 110 is provided, which emits, in operation, visible light 112. The first light emitting element 110 is, for example, a LED that is provided on a LED mounting board 214. At another side of the LED mounting board 214, another LED mounting board 214 is provided, which comprises a second light source 108, which emits UV light in a spectral range from 280 nm to 350 nm at a direction away from the light exit window 102. An angle, between a direction of a light beam of the visible light 112 (as emitted by the first light emitting element 110) and a direction of a light beam of UV light 106 (as emitted by the second light source 108), is about 180 degrees—this angle may also be smaller, for example, between 180 degrees and 120 degrees. An important aspect is that the UV light 106 is not emitted directly towards the light exit window 102. Opposite to the second light source 108, a reflection element 216 is provided. The reflection element 216 is capable of reflecting the UV light 106. The reflection element 216 is arranged such that the UV light 106, emitted by the second light source 108, is, at least, partially reflected towards the light exit window 102. In practical embodiments, the arrangement shown in FIG. 2a may be provided in a housing, such as, for example, the housing 104 of FIG. 1. The reflection element 216 is, for example, made of Aluminium or Boron nitride. The reflection element may also be a dichroic reflector. The reflection element 216 may also be a support panel provided with a layer of such material and this layer faces the second light source 108. The reflection element 216 may be specularly reflective or diffusely reflective. An advantage of a diffusely reflective reflection element 216 is that the UV light 106 is spread among a large number of light emission angles and, as such, it results in an even more safe lighting assembly 200.

The amount of emitted UV light 106 is relatively low to prevent possible health risks. However, close to the second light source 108, the irradiance (light energy per area unit, watt per square meter) of UV light 106 may be relatively high. In the context of the embodiment of FIG. 1a, it might be that, as a result of misuse, the human naked eye or other sensitive parts of the human body may come very close to the second light source 108 and receive this high irradiance, and thereby, causing possible damage. When the light emitted by the second light source 108 is reflected, at least, once, the light beam emitted by the second light source 108 becomes, at least, several times wider (seen in a cross-sectional view taken in a plane oriented perpendicular to the light beam) than directly at the light emitting surface of the second light source 108, and thereby, the irradiance reduces quite a lot. Thus, by forcing that the UV light 106 is not directly emitted into the ambient via the light exit window 102, but is only emitted into the ambient after, at least, one reflection, the lighting assembly 200 is safer under misuse conditions.

The amount of UV light 106 emitted by the second light source 108, the relative position of the second light source 108 with respect to the reflection element 216 and also with respect to the light exit window 102, determines the irradiance of the UV light at the light exit window 102. Because of some optical effects, the irradiance may vary along the light exit window. The relative positions of the second light source, the reflection element, and the light exit window are selected such that the irradiance of the UV light in the spectral range remains below $10^{-3}$ W/m$^2$ along the whole light exit window. Optionally, the second light source is switched off after an operational time of 15 minutes and is switched on again when the whole lighting assembly is switched on (after a period of being switched off). This switching off may be used to reduce the received UV dose significantly when, for example, the yearly received dose seems to exceed a yearly critical dose. By emitting UV light during at least 15 minutes, each person present in the space where the lighting assembly is used may receive at least a dose of UV light for stimulating Vitamin D production.

FIG. 2b schematically presents an embodiment of a lighting assembly 230 that is similar to the embodiment of FIG. 2a. In the lighting assembly 230, both the second light source 108 and the first light emitting element 110 emit a light beam in the direction of the light exit window 102. The second light source 108 and the first light emitting element 110 are provided on a LED mounting support 214, which are provided on a reflective element 216 that is capable of reflecting the UV light 106. In between both the second light source 108 and the first light emitting element 110 at one side, and the light exit window 102 at the other side, a dichroic mirror 232 is provided. The dichroic mirror 232 is capable of transmitting the visible light 112 and is also capable of reflecting the UV light 106. Thus, the visible light 112 is transmitted through the dichroic mirror 232 towards the light exit window 102 and the UV light 106 is reflected by the dichroic mirror 232 towards the reflection element 216, and the reflection element 216 reflects, at least, a portion of the UV light 106 towards the light exit window 102. Thereby, the UV light 106 is reflected twice resulting in a large reduction in the irradiance of the UV light 106 at the light exit window. Hence, lighting assembly 230 becomes a relatively safer lighting assembly.

FIG. 2c schematically presents an embodiment of a lighting assembly 260 that is similar to the lighting assembly 230. A difference between the lighting assembly 260 and lighting assembly 230 is that the first light emitting element 110 of FIG. 2b, in the context of lighting assembly 260, is a luminescent element 262 which is provided on a light emitting surface of the second light source 108. The luminescent element 262 comprises one or more luminescent materials and the specific configuration of luminescent materials is capable of absorbing a portion of the UV light 106 emitted by the second light source 108 and converting the absorbed light towards the visible light 112. Thus, only one type of light source is required, namely, one that emits UV light 106. In the lighting assembly 260, the luminescent element 262 does not absorb all UV light 106 emitted by the second light source 108 and, similar to the embodiment of FIG. 2b, the remaining UV light 106 is reflected by the dichroic mirror 232 and the reflection element 216 towards the light exit window. Examples of luminescent materials for use in the above discussed context are: BaMgAl$_{10}$O$_{17}$:Eu$^{2+}$ Zn$_2$SiO$_4$Mn$^{2+}$, Y$_3$Al$_5$O$_{12}$:Ce$^{3+}$, Y$_2$O$_3$:Eu$^{3+}$ Ca(PO$_4$)$_3$(F,Cl):Sb$^{3+}$, Mn$^{2+}$.

Figure 3A:
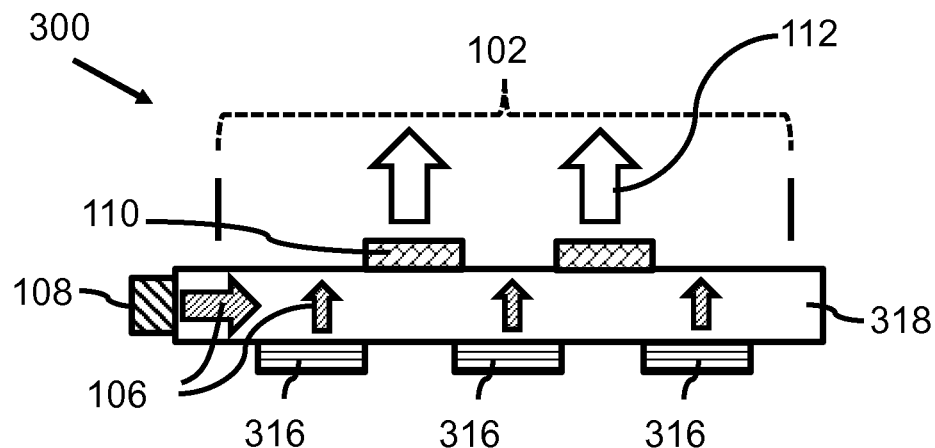
Figure 3B:
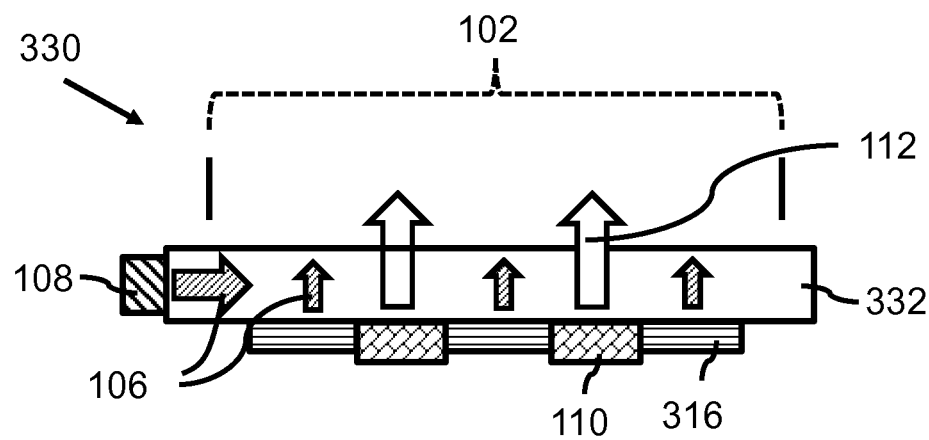
Figure 3C:
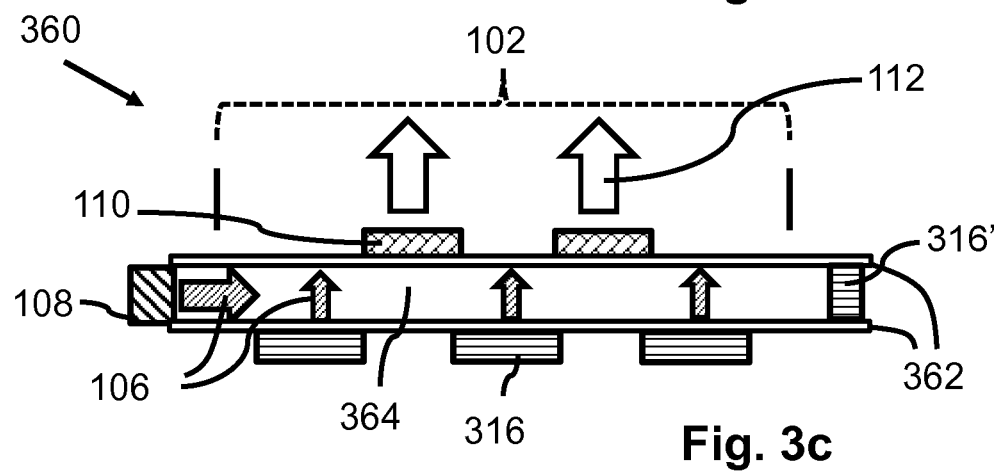

FIGS. 3a to 3c schematically present cross-sectional views of different embodiments of lighting assemblies 300, 330, 360.

In FIG. 3a, an embodiment of a lighting assembly 300 is presented that comprises, as a central element, a light guide 318 that is made of a (solid) material that is, at least, transparent for the UV light 106 in the spectral range from 280 nm to 350 nm. Optionally, the light guide 318 is also transparent for the visible light 112. A top surface of the light guide 318 is opposite to the light exit window 102. The light guide 318 is arranged substantially parallel to the light exit window 102. In other embodiments, the light guide 318 is not arranged parallel to the light exit window 102 and is arranged within the lighting assembly 300 such that the light that exits the light guide 318 is transmitted into the direction of the light exit window 102. On the top surface of the light guide 318, one or more first light emitting elements 110 are provided, which emit the visible light 112 towards the light exit window 102. At a bottom surface of the light guide, which is opposite to the top surface, one or more reflective elements 316 are provided that are capable of reflecting the UV light 106. The reflective elements 316 are further configured to change an angle of the rays of the UV light 106 such that the rays for which the angle has been changed are transmitted towards the light exit window 102. The reflective elements 316 are, for example, diffusely reflective for the UV light 106. As such, the reflective elements 316 act as light outcoupling structures. Also, other outcoupling elements can be used instead of the reflective elements 316. Also, irregularities at the bottom surface of the light guide 318 may assist in the outcoupling of the UV light 106 towards the light exit window 102. On at least one of the side surfaces of the light guide 318, which are outer surfaces in between the top surface and the bottom surface, the second light source 108 is provided and is arranged to emit a beam of the UV light 106 into the light guide 318. Thus, the direction of the beam of UV light 106 is substantially parallel to the top and bottom surface of the light guide 318. In this embodiment, the light guide 318 contributes to the reduction of the irradiance of the UV light 106 at the light exit window 102 compared to the irradiance of the UV light 106 directly at the light emitting surface of the second light source 108. The light is spread by the light guide 318 and the UV light 106 is reflected at least once inside the light guide 318. More than one second light source 108 may be provided at the side surfaces of the light guide 318. In the context of FIG. 3a, it has to be noted that lighting assembly 300 may be provided in a housing, for example, the housing 104 of FIG. 1a.

FIG. 3b presents a lighting assembly 330 similar to the lighting assembly 300 of FIG. 3a. In this embodiment, the light guide 332 is transparent for the visible light 112 and the UV light 106. A difference between the lighting assembly 300 and the lighting assembly 330 is that, in the lighting assembly 330, the first light emitting elements 110 are provided at the bottom surface of the light guide 332 and in between the reflective elements 316. The first light emitting elements 110 emit their light beams of visible light 112 in the light guide at a direction perpendicular to the bottom and top surface and, as such, towards the light exit window 102.

In this context, it is noted that in both the embodiments of FIGS. 3a and 3b, the first light emitting element may be a luminescent element which converts UV light 106 towards the visible light, or may be a first light source configured to emit the visible light 112. It is also noted that in another variation, the visible light 112 is also emitted from a side surface into the light guide and the reflective elements 316 (or other light outcoupling elements) are also configured to (diffusely) reflect the visible light 112. This may result in a thinner lighting assembly.

FIG. 3c presents a lighting assembly 360 similar to lighting assembly 300 of FIG. 3a. In this embodiment, the light guide 318 of FIG. 3a is replaced by a light guiding space 364, which is enclosed by two transparent plates 362. The UV light 106 is emitted into the space between the two transparent plates 362 and reflective elements 316 are used to outcouple the UV light 106 from the light guiding space 364 towards the light exit window 102. The sides of the lighting guiding space 364 are sealed by the second light source(s) 108 and some additional UV light reflective elements 316'.

Figure 4A:
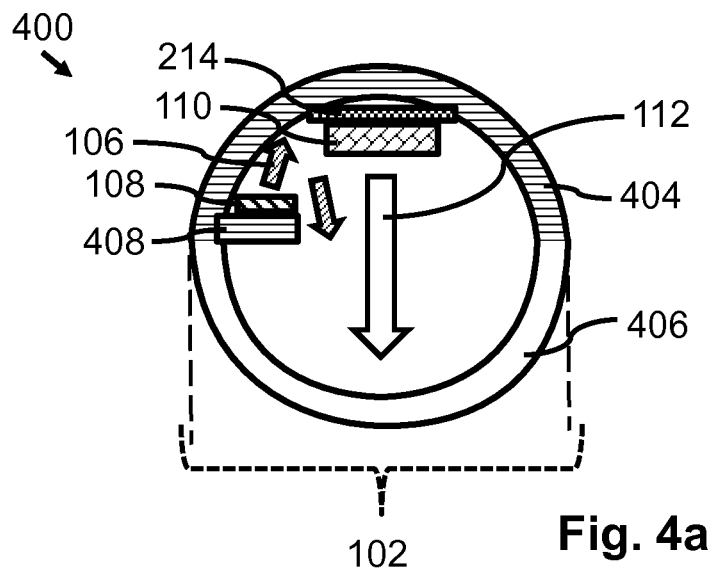
Figure 4B:
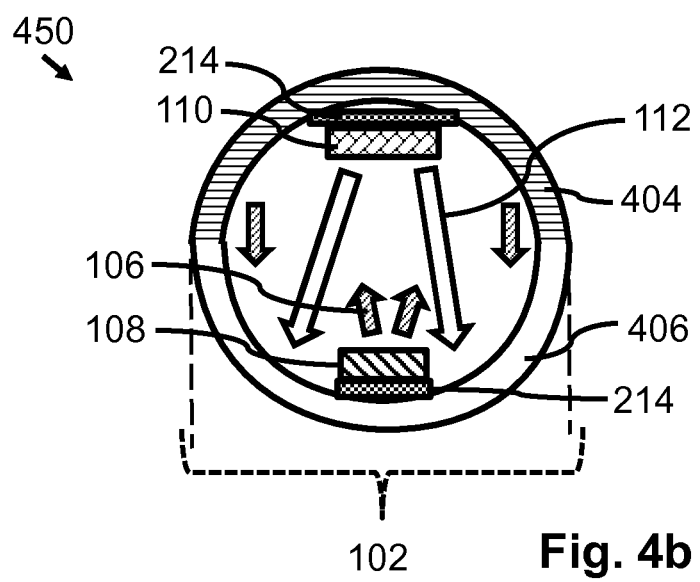

FIGS. 4a and 4b schematically present cross-sectional views of light tubes 400, 450 respectively, each comprising a lighting assembly. Both light tubes 400, 450 may be retrofit light tubes, which means that they fit in a traditional luminaire for fluorescent gas discharge tubes and that the retrofit light tube behaves like a traditional light tube. Each of the light tubes 400, 450 may also be a new type of light tube.

The light tube 400 of FIG. 4a comprises a tube, made, for example, of glass, quartz or a UV transparent plastic material e.g. silicone rubber. The cross-section shown in FIG. 4a is obtained along a plane perpendicular to the tube. The tube comprises, at least, a first portion 404 that is UV light reflective. The first portion 404 is provided, for example, with a UV light reflective coating. This UV light reflective coating may be provided at the inner surface of the tube or at the outer surface of the tube. The UV light reflective coating may be specularly reflective or diffusely reflective. The tube also comprises a second portion 406, which is capable of transmitting UV light 106 and visible light 112 into the ambient of the light tube 400. This means that the second portion is the light exit window 102. The second portion may be transparent or translucent for both types of light. Inside the tube, at a position about opposite to the second portion 406, one or more first light emitting elements 110 are provided (optionally provided on a LED mounting board 214). The first light emitting element 110 emits visible light directly into the direction of the second portion 406, and, thus, towards the light exit window. Inside the tube, for example, on one or more support panels 408 that are partially extending into the interior of the tube, one or more second light sources 108 are provided. The second light sources 108 emit, in operation, UV light 106 towards the first portion 404 of the tube and the first portion 404 reflects the UV light 106 towards the light exit window. Thus, the UV light 106 is reflected at least once and thereby, the irradiance of the UV light 106 at the light exit window is significantly reduced compared to the irradiance of the UV light 106 directly at the light emitting surface of the second light source(s) 108.

FIG. 4b presents a light tube 450 that is similar to the light tube 400 of FIG. 4a. An important difference between the light tube 450 and the light tube 400 is a different location of the second light source(s) 108. The second light source(s) 108 are not provided on one or more support panels 408 that extend partially into the tube, but are provided on a LED support panel 214 at a location inside the tube that is opposite to the location of the first light emitting element(s) 110. In operation, the UV light 106, emitted by the second light source(s) 108, is emitted towards the first portion 404 of the tube and subsequently reflected towards the second portion 406 (and, thus, the light exit window 102).

Figure 5A:
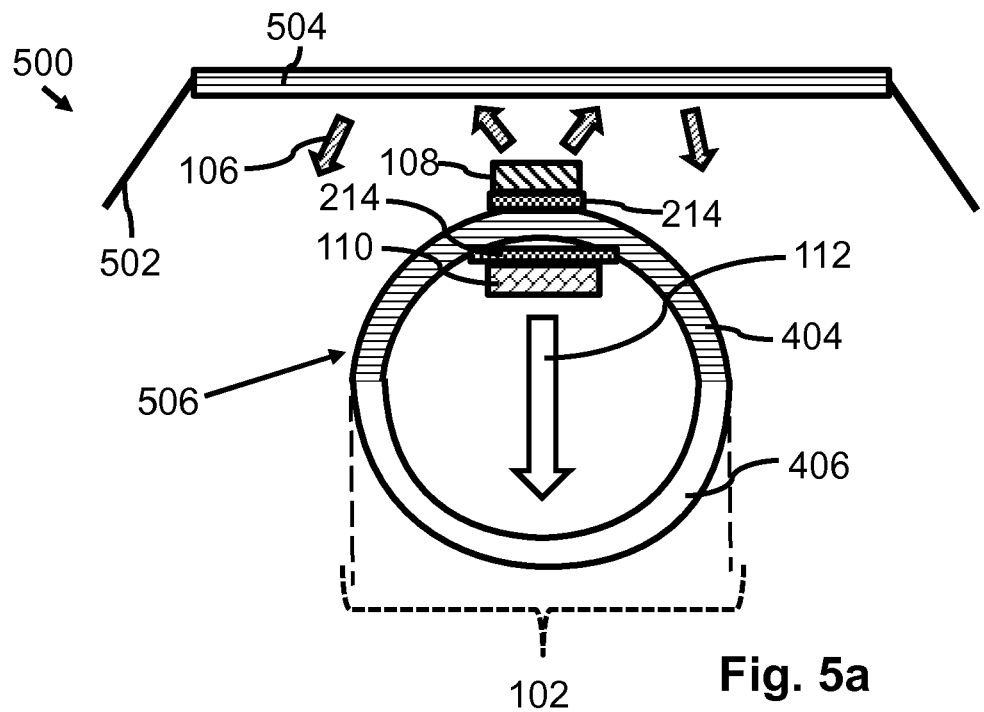

FIG. 5a schematically presents a cross-sectional view of a luminaire 500, which comprises a light tube 506. The presented light tube 506 is similar to the light tubes 400, 450 of FIGS. 4a, 4b. A difference between the light tube 506 and the light tubes 100,450 is that the second light source 108 is provided at the outer surface of the light tube 506. In FIG. 5a, the light tube 506 still comprises a first portion 404, which further comprises a UV reflective coating, and a second portion 406 which is light transmitting. In another embodiment, about the whole light tube 506 is transparent for, at least, visible light 112.

The luminaire 500 has a specific UV light reflective area 504. This UV light reflective area 504 is, optionally, surrounded by reflectors 502 which may be UV light reflective as well. The luminaire 500 is designed such that, when the light tube 506 is provided in the luminaire, the second light source 108 emits the UV light 106 towards the UV light reflective area 504. Thereby, the UV light 106 is reflected, at least, once and thereby the irradiance of the UV light 106 is significantly reduced.

Figure 5B:
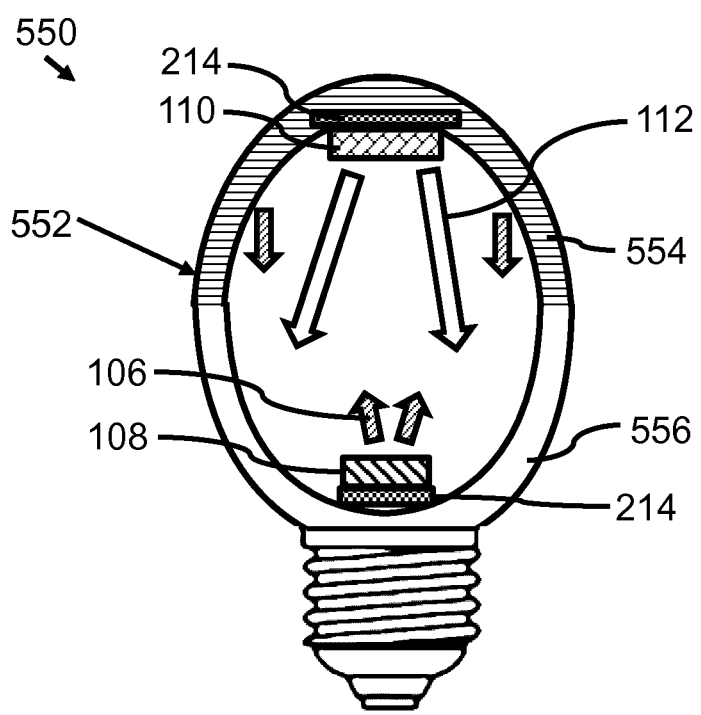

FIG. 5b schematically presents a cross-sectional view of a (possibly) retrofit light bulb 550. Seen in a cross-sectional view, the retrofit light bulb 550 has a similar design as the light tube 450 of FIG. 4b, however, the tube is replaced by a light bulb 552. Another difference, of course, is that the retrofit light bulb 550 has a light-bulb specific base that is suitable for receiving the power and coupling the retrofit light bulb 550 to a luminaire. The light bulb 552 comprises a first portion 554 that is provided with an UV light reflective coating (which may also be light reflective for visible light). The light bulb 552 also comprises a second portion 556, which is light transmitting for visible light 112 and for UV light 106. Inside the light bulb 552, the second light source 108 is arranged at a position where it is capable of emitting the UV light 106 towards the first portion 554. The first light emitting element 110 is arranged at a position where the visible light is emitted towards the second portion 556. In this embodiment of the retrofit light bulb 550, and also in the embodiment of the light tube 450 of FIG. 4*b*, the first light emitting element 110 may be a first light source (e.g. LED) or a luminescent element because the first light emitting element also receives a significant portion of the UV light 106 emitted by the second light source 108. The embodiments of FIGS. 4*a*, 4*b* and 5*b* are embodiments of a lamp.

Figure 6A:
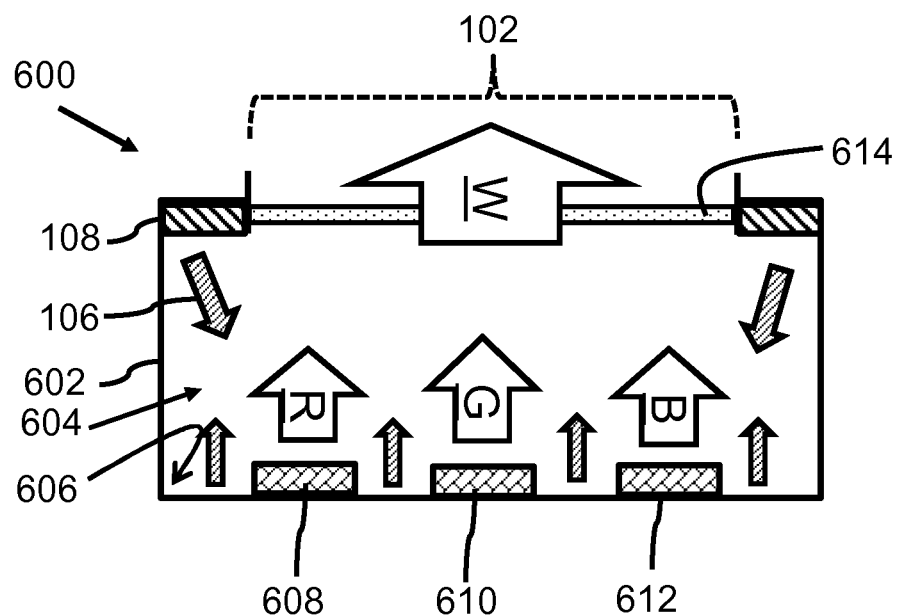

FIG. 6*a* schematically presents a cross-sectional view of a lighting assembly 600, which comprises a light mixing chamber 604. The light mixing chamber 604 is enclosed by a housing 602 and comprises a light exit window 102. Optionally, at the light exit window, the housing 604 has a transparent plate 614, or a translucent plate 614 that acts as a diffusor. A portion of or all walls 606 of the housing that face the light mixing chamber 604 are UV light reflective and may also be reflective for visible light. A specific coating/layer may be provided on the walls 606 to obtain this effect. The walls 606 that face the light mixing chamber 604 may be specularly reflective or diffusely reflective. In the example of FIG. 6*a*, two second light sources 108 are provided in the interior of the light mixing chamber 604 at a position adjacent to the light exit window. The second light sources 108 are arranged to emit their UV light 106 into the light mixing chamber 604 and not directly to the light exit window 102. Then the walls 606 of the light mixing chamber 604 reflect the UV light 106 at least once before it is transmitted through the light exit window 102 into the ambient of the lighting assembly 600. The light mixing chamber 604 may also have one or more first light emitting elements as discussed previously and these one or more first light emitting elements are arranged to emit their visible light directly (or also indirectly via reflections) towards the light exit window. In the example of FIG. 6*a*, the first light emitting element comprises three different Light Emitting Diodes (LEDs) 608, 610, 612 that are arranged to emit red light R, green light G and blue light B, respectively. In operation they receive a certain amount of power such that the combination of the red light R, the green light G and the blue light B forms the relatively white light W that has, as discussed previously, a color point in a CIE XYZ color space and the color point has a distance smaller than 25 SDCM to the black body line in that color space. In the embodiment of FIG. 6*a*, the walls 606 are also reflective for visible light, and thereby, contributing to the mixing of the red light R, the green light G and the blue light B.

Figure 6B:
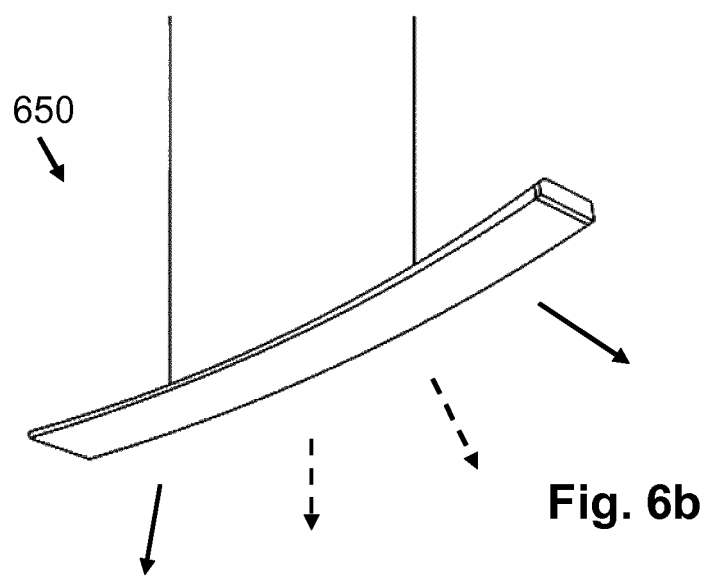

FIG. 6*b* schematically presents a three dimensional view of a luminaire 650. The luminaire 650 comprises one of: one of the lighting assemblies 100, 200, 230, 260, 300, 330, 360, 600 of FIG. 1, FIGS. 2*a*-2*c*, FIGS. 3*a*-3*c*, FIG. 6, respectively, and one of the light tubes 400, 450 of FIGS. 4*a*, 4*b*, respectively, or the retrofit light tube 550 of FIG. 6*b*. The luminaire 650 may also have a construction like the luminaire of FIG. 5*a*.

Figure 7:
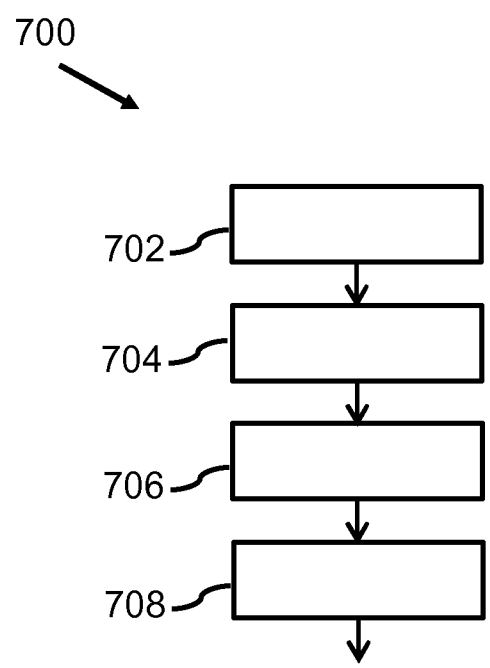

FIG. 7 schematically presents a method 700 of illuminating a space. The method 700 comprises: (i) providing 702 a lighting assembly comprising a light exit window for emitting light into an ambient of the lighting assembly, a first light emitting element for emitting visible light, and a second light source for emitting UV light, the first light emitting element being capable of emitting visible light having a color point in a CIE XYZ color space, the color point having a distance smaller than 25 SDCM to the black body line in said color space, the UV light comprising light in a spectral range from 280 nm to 350 nm, ii) emitting 704 a safe amount of UV light in the spectral range through the light exit window, the safe amount of the UV light has a first radiant flux, the UV light is not emitted directly towards the light exit window, iii) reflecting 706 at least a portion of the emitted UV light towards the light exit window, iv) emitting 708 a second radiant flux of the visible light through the light exit window, a ratio between a first radiant flux and a second radiant flux is in a range from 0.01 to 0.0001.

In summary, a lighting assembly, a lamp, a retrofit light bulb, a retrofit light tube, a luminaire and a method of illuminating a space are provided. The lighting assembly comprises a first light emitting element and a second light source. The first light emitting element is for emitting visible light having a color point close to the black body line. The second light emitting element emits UV light in a spectral range from 280 nm to 350 nm. The lighting assembly is configured to emit, in operation, a safe amount of the UV light in the spectral range through a light exit window. A ratio between a first radiant flux of the UV light and a second radiant flux of the visible light is in a range from 0.01 to 0.0001.

It is to be noted that the invention may be implemented in hardware and/or software, using programmable components. A method for implementing the invention has the steps corresponding to the functions defined for the assembly as described with reference to FIG. 1*a*.

It will be appreciated that the above description for clarity has described embodiments of the invention with reference to different functional units. However, it will be apparent that any suitable distribution of functionality between different functional units may be used without deviating from the invention. Hence, references to specific functional units are only to be seen as references to suitable means for providing the described functionality rather than indicative of a strict logical or physical structure or organization.

It is noted, that in this document the word 'comprising' does not exclude the presence of other elements or steps than those listed and the word 'a' or 'an' preceding an element does not exclude the presence of a plurality of such elements, that any reference signs do not limit the scope of the claims, that the invention may be implemented by means of both hardware and software, and that several 'means' or 'units' may be represented by the same item of hardware. Further, the invention is not limited to the embodiments, and the invention lies in each and every novel feature or combination of features described above or recited in mutually different dependent claims.

The invention claimed is:

1. A lighting assembly for illumination, the lighting assembly comprising:
   a light exit window for emitting light into an ambient of the lighting assembly,
   a first light emitting element for emitting visible light, the first light emitting element being capable of emitting visible light having a color point in a CIE XYZ color space, the color point having a distance smaller than 25 SDCM to a black body line in said color space, the first light emitting element being arranged to emit the visible light directly towards the light exit window,
   a second light source for emitting UV light, the UV light having a spectral range from 280 nm to 350 nm, wherein the UV light is at least partly emitted through the light exit window, the second light source being arranged not to emit the UV light directly towards the light exit window, a reflection element configured to reflect the UV light, the reflection element being arranged at a position for receiving at least a portion of the UV light and is arranged for reflecting the received UV light towards the light exit window, wherein the lighting assembly is configured to emit an amount of the UV light in the spectral range through the light exit window, the amount of the UV light having a first radiant flux and the lighting assembly is configured to emit a second radiant flux of the visible light through the light exit window, a ratio between the first radiant flux and the second radiant flux is in a range from 0.01 to 0.0001.

2. A lighting assembly according to claim 1, wherein the first light emitting element comprises a first light source for emitting the visible light or comprises a luminescent element for converting a portion of the UV light to the visible light.

3. A lighting assembly according to claim 2, wherein relative positions of the second light source, the reflection element, and the light exit window are selected such that an irradiance of the UV light in the spectral range remains below $10^{-3}$ W/m$^2$ along the whole light exit window.

4. A lighting assembly according to claim 1 comprising a dichroic mirror being configured to reflect the UV light and being configured to transmit the visible light, the dichroic mirror being arranged at a mirror position to prevent direct emission of UV light from the second light source through the light exit window.

5. A lighting assembly according to claim 1, wherein a smallest angle between a second direction of a second light beam emitted by the second light source and a first direction of a first light beam emitted by the first light emitting element is between 90 degrees and 180 degrees, or alternatively, between 120 degrees and 180 degrees.

6. A lighting assembly according to claim 1 comprising a light mixing chamber at least partially enclosed by walls, wherein at least a portion of the walls is UV light reflective.

7. A lighting assembly according to claim 1, comprising a light guiding space being arranged substantially parallel to the light exit window, the light guiding space having at least one UV light outcoupling element at a wall opposite to the light exit window, the second light source being arranged to emit a UV light beam into the light guiding space at a direction substantially parallel to the light exit window.

8. A lighting assembly according to claim 1, wherein the second light source emits at least 60% of the emitted radiation in the spectral range from 300 nm to 320 nm.

9. A lamp for illumination comprising the lighting assembly according to claim 1.

10. A retrofit light bulb for illumination, the retrofit light bulb comprising a light transmitting bulb and the lighting assembly according to claim 1, wherein the light transmitting bulb comprising an UV light reflective layer at a first portion of the light transmitting bulb and the light transmitting bulb having a second portion through which the visible light and the UV light are transmitted into the ambient, wherein the second light source is arranged to emit the UV light only towards the first portion, the UV light reflective layer being the reflection element.

11. A retrofit light tube for illumination, the retrofit light tube comprising a light transmitting tube and the lighting assembly according to claim 1, wherein the light transmitting tube comprising a UV light reflective layer at a first portion of the light transmitting tube and the light transmitting tube having a second portion through which the visible light and the UV light are transmitted into the ambient, wherein the second light source is arranged to emit the UV light only towards the first portion, the UV light reflective layer being the reflection element.

12. A luminaire for illumination comprising the lighting assembly according to claim 1.

13. A method of illuminating a space, the method comprising:
providing a lighting assembly comprising a light exit window for emitting light into an ambient of the lighting assembly, a first light emitting element for emitting visible light directly towards the light exit window, and a second light source for emitting UV light, the first light emitting element being capable of emitting visible light having a color point in a CIE XYZ color space, the color point having a distance smaller than 25 SDCM to a black body line in said color space, the UV light comprising light in a spectral range from 280 nm to 350 nm,
emitting an amount of UV light in a spectral range through the light exit window, wherein the amount of the UV light has a first radiant flux, and the UV light is not emitted directly towards the light exit window,
reflecting at least a portion of the emitted UV light towards the light exit window, and
emitting a second radiant flux of the visible light through the light exit window, a ratio between the first radiant flux and the second radiant flux is in a range from 0.01 to 0.0001.

* * * * *